US00PP17885P2

(12) United States Plant Patent
Barnes

(10) Patent No.: US PP17,885 P2
(45) Date of Patent: Jul. 31, 2007

(54) ***AGLAONEMA* PLANT NAMED 'DECORA'**

(50) Latin Name: ***Aglaonema* hybrid**
Varietal Denomination: Decora

(75) Inventor: James Glenn Barnes, Tavares, FL (US)

(73) Assignee: Green Star Foliage, Inc., Apopka, FL (US)

( * ) Notice: Subject to any disclaimer, the term of this patent is extended or adjusted under 35 U.S.C. 154(b) by 0 days.

(21) Appl. No.: 11/351,846

(22) Filed: Feb. 10, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Aglaonema* plant named 'Decora', characterized by its upright and outwardly arching plant form; compact growth habit; freely clumping habit; full, dense and bushy appearance; upper leaf surfaces green and silver in color; undulate leaf margins; and tolerance to low temperatures.

3 Drawing Sheets

Botanical designation: *Aglaonema* hybrid.
Cultivar denomination: 'Decora'.

BACKGROUND OF THE INVENTION

The present Invention relates to a new and distinct cultivar of *Aglaonema* plant, botanically known as *Aglaonema* hybrid and hereinafter referred to by the name 'Decora'.

The new *Aglaonema* is the result of a planned breeding program conducted by the Inventor in Apopka, Fla. The objective of the breeding program is to create new compact *Aglaonema* cultivars with resistance to pathogens and pests.

The new *Aglaonema* originated from a cross-pollination made by the Inventor in June, 2000, of an unnamed selection of the *Aglaonema* hybrid cultivar Silver Bay, not patented, as the female, or seed, parent with the *Aglaonema* hybrid cultivar Emerald Beauty, disclosed in U.S. Plant patent application Ser. No. 13,824, as the male, or pollen, parent. The new *Aglaonema* was discovered and selected by the Inventor in June, 2000 as a single plant within the progeny of the stated cross-pollination in a controlled environment in Apopka, Fla.

Asexual propagation of the new cultivar by cuttings since September, 2002 in a controlled environment in Apopka, Fla. has shown that the unique features of this new *Aglaonema* are stable and reproduced true to type in successive generations.

SUMMARY OF THE INVENTION

The following traits have been repeatedly observed and are determined to be the unique characteristics of 'Decora'. These characteristics in combination distinguish 'Decora' as a new and distinct cultivar of *Aglaonema:*

1. Upright and outwardly arching plant form.
2. Compact growth habit.
3. Freely clumping habit; full, dense and bushy appearance.
4. Upper leaf surfaces green and silver in color.

5. Undulate leaf margins.
6. Tolerant to low temperatures.

In side-by-side comparisons conducted by the Inventor in Apopka, Fla., plants of the new *Aglaonema* differed from plants of the female parent selection, in the following characteristics:

1. Plants of the new *Aglaonema* were more compact and denser than plants of the female parent selection.
2. Plants of the new *Aglaonema* had shorter internodes than plants of the female parent selection.
3. Plants of the new *Aglaonema* had narrower leaves with more undulate margins than plants of the female parent selection.
4. Plants of the new *Aglaonema* and the female parent selection differed in leaf coloration.
5. Plants of the new *Aglaonema* were more cold temperature-tolerant than plants of the female parent selection.

In side-by-side comparisons conducted by the Inventor in Apopka, Fla., plants of the new *Aglaonema* differed from plants of the male parent, the cultivar Emerald Beauty, in the following characteristics:

1. Plants of the new *Aglaonema* were more compact and denser than plants of the cultivar Emerald Beauty.
2. Leaves of plants of the new *Aglaonema* had more undulate margins than leaves of plants of the cultivar Emerald Beauty.
3. Plants of the new *Aglaonema* and the cultivar Emerald Beauty differed in leaf coloration.

Plants of the new *Aglaonema* can be compared to plants of the cultivar Jubilee, disclosed in U.S. Plant Pat. No. 10,270. In side-by-side comparisons conducted in Apopka, Fla., plants of the new *Aglaonema* differed from plants of the *Aglaonema* cultivar Jubilee in the following characteristics:

1. Plants of the new *Aglaonema* were more compact, denser and more arching than plants of the cultivar Jubilee.
2. Plants of the new *Aglaonema* had shorter internodes than plants of the cultivar Jubilee.

3. Plants of the new *Aglaonema* had narrower leaves with more undulate margins than plants of the cultivar Jubilee.
4. Plants of the new *Aglaonema* and the cultivar Jubilee differed in leaf coloration.
5. Plants of the new *Aglaonema* were more cold temperature-tolerant than plants of the cultivar Jubilee.

BRIEF DESCRIPTION OF THE PHOTOGRAPHS

The accompanying colored photographs illustrate the overall appearance of the new *Aglaonema,* showing the colors as true as it is reasonably possible to obtain in colored reproductions of this type. Colors in the photographs may differ slightly from the color values cited in the detailed botanical description which accurately describe the colors of the new *Aglaonema.*

The photograph on the first sheet comprises a top perspective view of a typical plant of 'Decora' grown in a container.

The photographs on the second page are close-up views of upper and lower surfaces of developing leaves (bottom of sheet) and fully expanded leaves (top of sheet) of 'Decora'.

The photograph on the third sheet comprises a side perspective view of typical plants of 'Jubilee' (left) and 'Decora' (right).

DETAILED BOTANICAL DESCRIPTION

The cultivar Decora has not been observed under all possible environmental conditions. The phenotype may vary somewhat with variations in environment such as temperature and light intensity without, however, any variance in genotype. The following observations and measurements describe plants of the new *Aglaonema* that were grown in 25-cm containers, in Apopka, Fla., in a fiberglass and polyethylene-covered greenhouse with light levels about 1,800 footcandles. During the production of the plants, day temperatures ranged from about 21° C. to about 35° C. and night temperatures ranged from about 10° C. to about 14° C. Plants used for the photographs and description were about nine months from planting. Color references are made to The Royal Horticultural Society Colour Chart, 2001 Edition, except where general terms of ordinary dictionary significance are used.

Botanical classification: *Aglaonema* hybrid cultivar Decora.

Parentage:

*Female, or seed, parent.*—Unnamed selection of *Aglaonema* hybrid cultivar Silver Bay, not patented.

*Male, or pollen, parent.*—*Aglaonema* hybrid cultivar Emerald Bay, disclosed in U.S. Plant Pat. No. 13,824.

Propagation:

*Type.*—By cuttings.

*Time to initiate roots, summer.*—About 10 days at 29° C.

*Time to initiate roots, winter.*—About 21 days at 19° C.

*Time to produce a rooted plant, summer.*—About 45 days at 29° C.

*Time to produce a rooted plant, winter.*—About 70 days at 19° C.

*Root description.*—Thick, fleshy; white in color.

*Rooting habit.*—Moderately branching; moderately dense.

Plant description:

*Plant form.*—Erect when young, becoming outwardly arching as leaves develop; inverted triangle, symmetrical and uniform.

*Growth habit.*—Compact growth habit. Plant size appropriate for 15-cm to 25-cm containers.

*Growth habit.*—Freely clumping habit; plants typically produce about five offshoots per plant; full, dense and bushy appearance.

*Plant height.*—About 27 cm.

*Plant width* (*spread*).—About 58 cm.

*Stem description.*—Length: About 12 cm. Diameter: About 1.5 cm. Internode length: About 1.35 cm. Aspect: Upright. Strength: Sturdy; somewhat flexible. Texture: Smooth, glabrous. Color, immature: 145C. Color, mature: 148A tinged with 162C.

*Foliage description.*—Arrangement: Alternate; single. Length: About 21 cm. Width: About 5.5 cm. Shape: Ovate to elliptic. Apex: Acuminate. Base: Obtuse. Margin: Entire; undulating. Texture, upper and lower surfaces: Smooth, glabrous; leathery, thick. Venation pattern: Pinnate. Color: Developing leaves, upper surface: Center, 194C, with random areas of 191A to 191B; towards the margins, 137A to lighter and more green than 147A; random marginal flecks, 194C. Developing leaves, lower surface: Darker and greener than 146B. Fully expanded leaves, upper surface: Center, 191C to 191D, with faint areas of 191A; towards the margins, darker and more green than 147A; random marginal flecks, 191C to 191D. Fully expanded leaves, lower surface: Greener than 147A. Venation, upper surface: Midvein, immature: 194C tinged with 138B. Midvein, mature: 191A. Lateral veins: Similar to lamina. Venation, lower surface: Midvein, immature: 147B to 147C. Midvein, mature: 147B. Lateral veins: 147A. Petiole: Aspect: Initially upright; when mature, about 40° from vertical; base, clasping. Length: About 9.4 cm. Diameter, distal: About 4.5 cm. Diameter, proximal: About 1.6 cm. Color: 147B; towards the base, 145C. Wing length: About 6.9 cm. Wing diameter: About 7 mm. Wing color, outer surface: 147B. Wing color, inner surface: 147C to 147D.

Flower description: Flower development has not been observed on plants of the new *Aglaonema.*

Disease/pest resistance: Plants of the new *Aglaonema* have not been observed to be resistant to pathogens and pests common to *Aglaonema.*

Temperature tolerance: Plants of the new *Aglaonema* have been observed to be tolerant to temperatures ranging from about 7° C. to about 37° C.

It is claimed:

1. A new and distinct cultivar of *Aglaonema* plant named 'Decora', as illustrated and described.

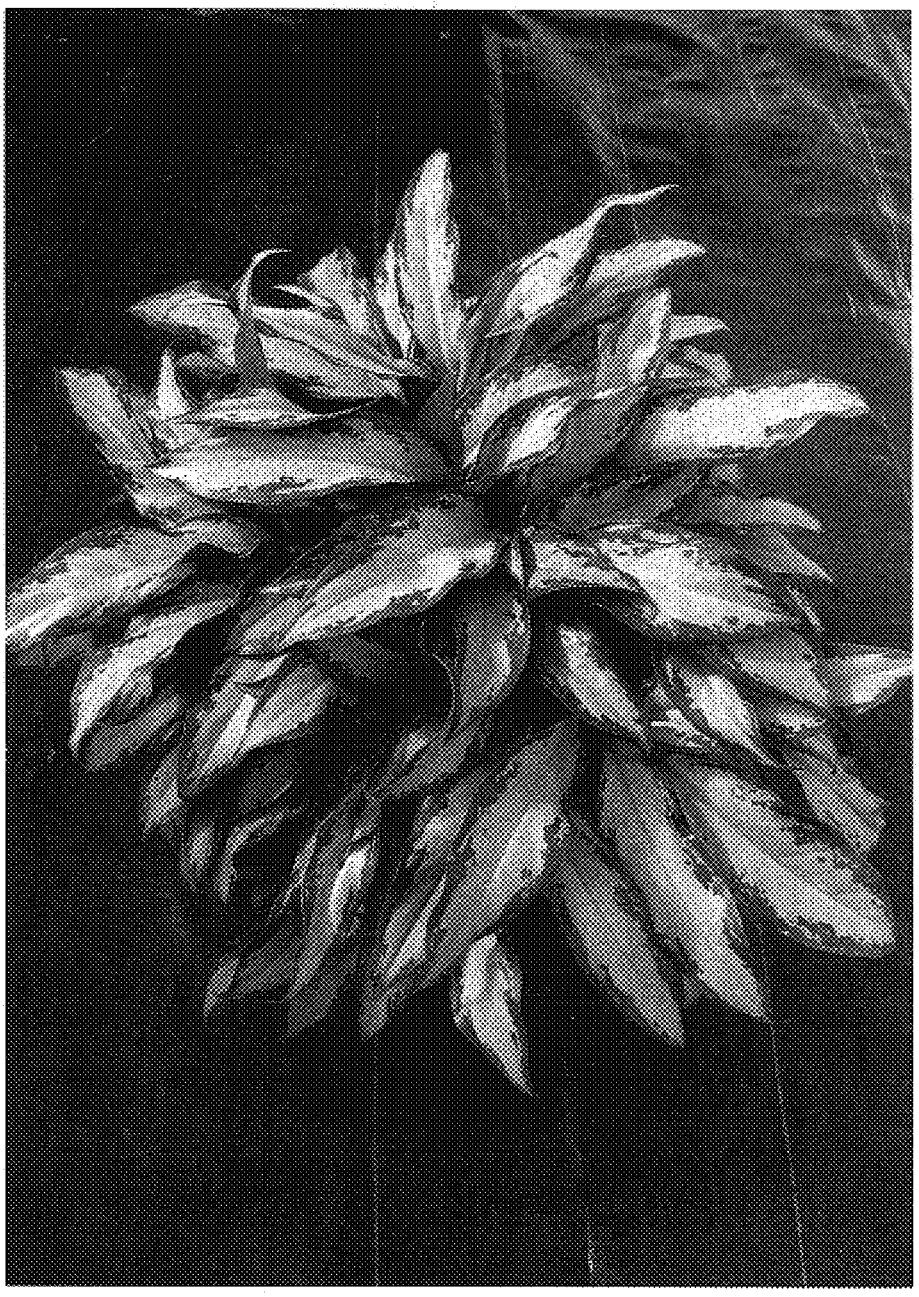

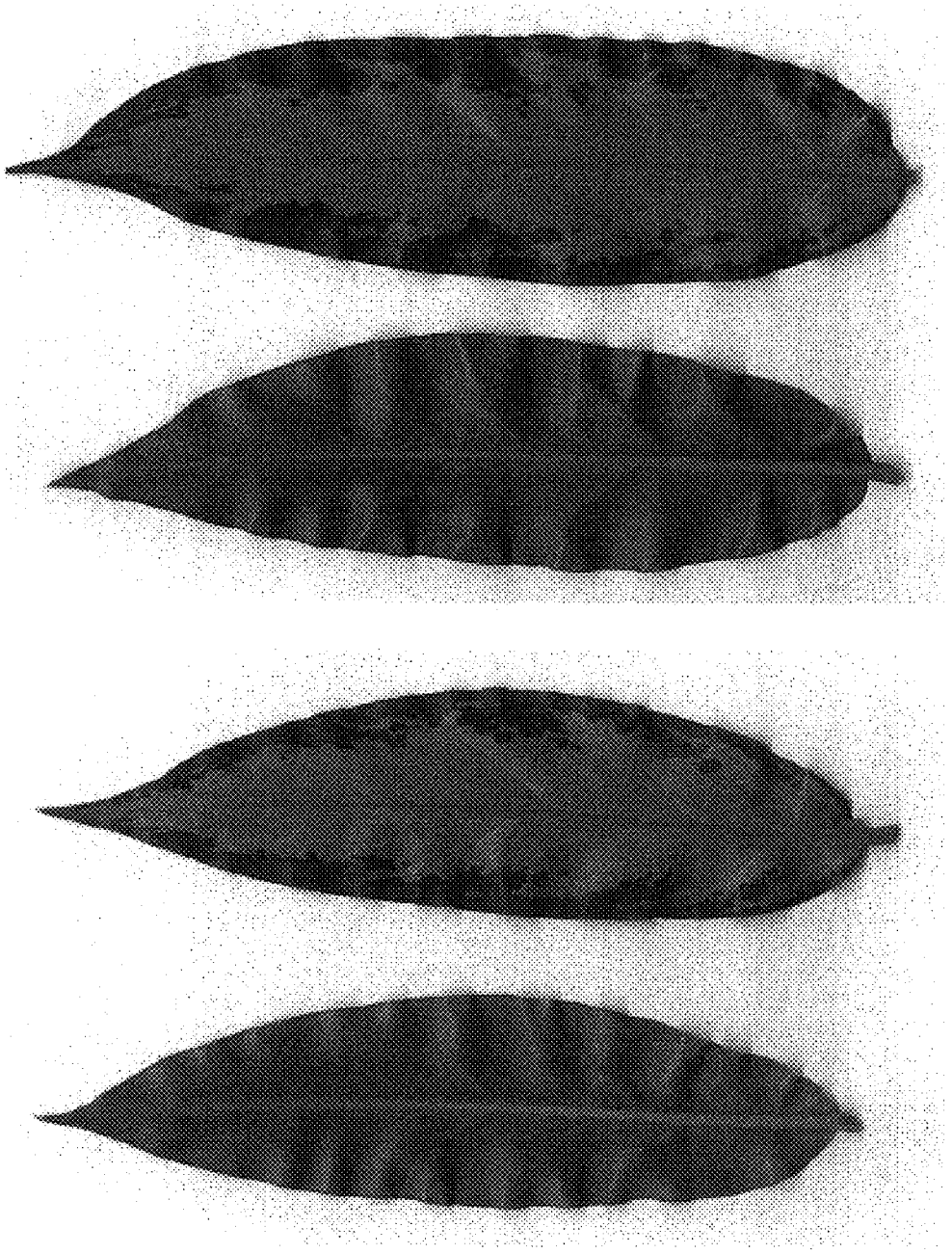

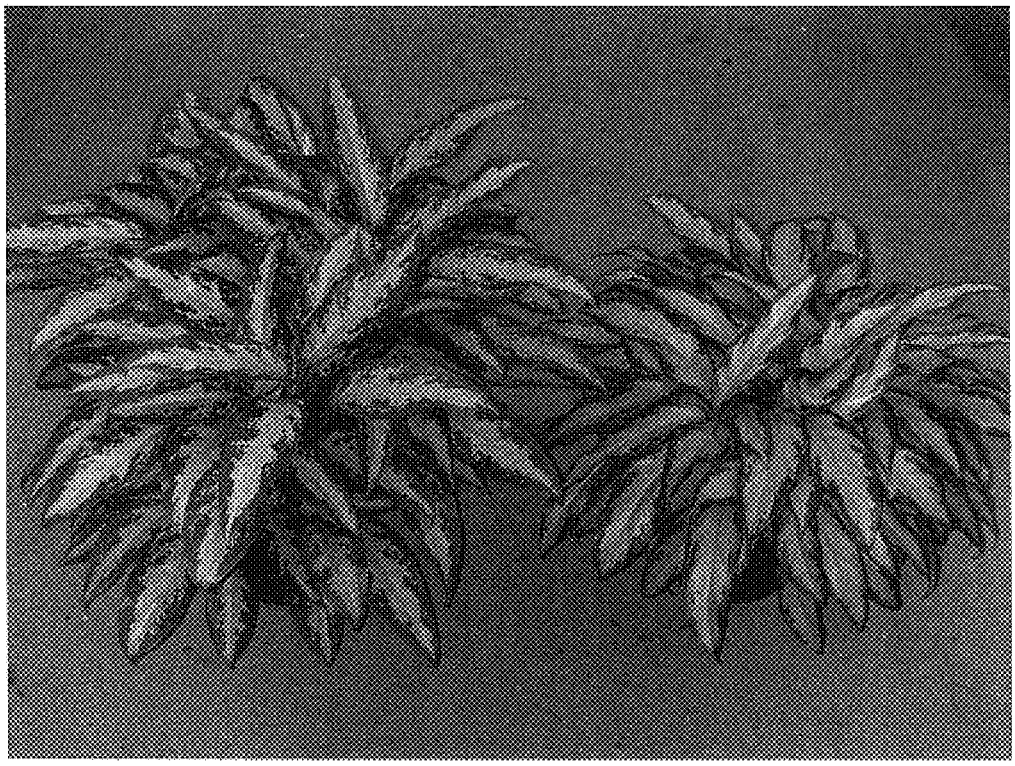

* * * * *